(12) United States Patent
Saudan et al.

(10) Patent No.: US 11,390,575 B2
(45) Date of Patent: Jul. 19, 2022

(54) ISOMERISATION REACTION

(71) Applicant: FIRMENICH SA, Satigny (CH)

(72) Inventors: Lionel Saudan, Satigny (CH); Julie Quintaine, Satigny (CH)

(73) Assignee: FIRMENICH SA, Satigny (CH)

(*) Notice: Subject to any disclaimer, the term of this patent is extended or adjusted under 35 U.S.C. 154(b) by 0 days.

(21) Appl. No.: 17/281,504

(22) PCT Filed: Mar. 17, 2020

(86) PCT No.: PCT/EP2020/057206
§ 371 (c)(1),
(2) Date: Mar. 30, 2021

(87) PCT Pub. No.: WO2020/187877
PCT Pub. Date: Sep. 24, 2020

(65) Prior Publication Data
US 2022/0041536 A1 Feb. 10, 2022

(30) Foreign Application Priority Data

Mar. 21, 2019 (EP) ..................................... 19164342

(51) Int. Cl.
*C07C 45/67* (2006.01)
*B01J 31/28* (2006.01)

(52) U.S. Cl.
CPC ............... *C07C 45/67* (2013.01); *B01J 31/28* (2013.01)

(58) Field of Classification Search
CPC .................................. C07C 45/67; B01J 31/28
See application file for complete search history.

(56) References Cited

PUBLICATIONS

International Search Report and Written Opinion for corresponding PCT/EP2020/057206 dated Apr. 9, 2020, 13 pages.
Ronald F. Childs et al. Journal of Organic Chemistry, vol. 49, No. 23, published 1984, pp. 4352-4358.

*Primary Examiner* — Sikarl A Witherspoon
(74) *Attorney, Agent, or Firm* — Armstrong Teasdale LLP

(57) ABSTRACT

Described herein is a process including isomerizing the β position of a β-trisubstituted $C_3$-$C_{70}$ carbonyl compound.

15 Claims, No Drawings

US 11,390,575 B2

ISOMERISATION REACTION

CROSS-REFERENCE TO RELATED APPLICATIONS

This application is a U.S. National Phase Application of International Patent Application No. PCT/EP2020/057206, filed Mar. 17, 2020, which claims the benefit of priority to European Patent Application No. 19164342.8, filed Mar. 21, 2019, the entire contents of which are hereby incorporated by reference herein.

TECHNICAL FIELD

The present invention relates to the field of organic synthesis and more specifically to the isomerization of the β position of a β-trisubstituted $C_3$-$C_{70}$ carbonyl compound.

PRIOR ART

The access to compounds having a specific stereochemistry is highly sought. One of the methods leading to obtain stereo enriched compounds is the hydrogenation. However, available hydrogenation method to obtained trans substituted cycloalkane or cycloalkanone compound are very limited. In particular, trans-decalone compounds, despite the fact that they represent skeletons highly desirables as they can be useful as perfuming ingredients or as starting material for the construction of compounds having a more complex skeleton, are mainly obtained by the reduction of the corresponding enone using Birch conditions. However, said conditions are difficult to implement under large scale for safety and environmental reason. Even if recently, the trans-selective reduction of cyclohexene to favor the thermodynamic product using cobalt and manganese catalyst reported in *Journal of American Chemical society* 2014, 1300 has been reported, said method requests to prepare the reductant which could be difficult to handle under large scale.

So, there is a need to develop a safer and cleaner methodology to the access of such compounds.

The present invention provides a solution to the above problem by performing an isomerization reaction allowing modifying the configuration at the β position of a β-trisubstituted $C_3$-$C_{70}$ carbonyl compound. To the best of our knowledge, in the prior art there is no report of an isomerization process as disclosed in the present invention.

SUMMARY OF THE INVENTION

The invention relates to a novel method allowing favoring the formation of the most thermodynamic product through isomerization conditions. Said method allows avoiding Birch reduction conditions or unusual catalysts.

So, a first object of the present invention is a process for the isomerization of a β-trisubstituted $C_3$-$C_{70}$ carbonyl compound to modify the configuration of the trisubstituted β position, characterized in that said process is carried out in the presence of a photoredox catalyst, a hydrogen atom transfer donor, an amine and light.

DESCRIPTION OF THE INVENTION

It has now been discovered that the stereochemistry of the β position of a carbonyl compound may be isomerized combining enamine formation, photoredox catalyst and hydrogen atom donor.

The object of the present invention is a process for the isomerization of a β-trisubstituted $C_3$-$C_{70}$ carbonyl compound to modify the configuration of the trisubstituted β position, characterized in that said process is carried out in the presence of a photoredox catalyst, a hydrogen atom transfer donor, an amine and light.

For the sake of clarity, by the expression "isomerization of a β-trisubstituted $C_3$-$C_{70}$ carbonyl compound to modify the configuration of the trisubstituted β position", or the similar, it is meant the normal meaning in the art; i.e. the configuration of the carbon in β position of the carbonyl functional group will be modified and the invention's process allows enhancing the amount of one enantiomer or diastereoisomer. The invention's process is a process to enrich the amount of one enantiomer or diastereoisomer. In other words, the configuration of the carbon in β position of the carbonyl functional group may be switch between racemic and R, between racemic and S, between S and R or between R and S; i.e. the isomerization is an epimerization. According to another particular embodiment, the configuration of the carbon in β position of the carbonyl functional group may be switch between R and a 50:50 mixture of R and S or between S and a 50:50 mixture of R and S; i.e. the isomerization is a racemization. The invention's process allows obtaining the most thermodynamically stable enantiomer or diastereoisomer. Particularly, the isomerization is an epimerization; i.e. the β-trisubstituted $C_3$-$C_{70}$ carbonyl compound possesses two or more chiral centers and only the configuration of the β position is modified.

By "configuration", it is meant the normal meaning in the art; i.e. the spatial arrangement of a stereogenic center. The configuration may be absolute or relative.

For the sake of clarity, by the expression "enantiomer or diastereomer", or the similar, it is meant the normal meaning understood by a person skilled in the art, i.e. the carbonyl compound may possess several stereocenters and each of said stereocenters can have two different stereochemistries (e.g. R or S). The carbonyl compound may even be in the form of a pure enantiomer or in the form of a mixture of enantiomers or diastereoisomers. The carbonyl compound can be in a racemic form or scalemic form. The invention's process allows, starting from a carbonyl compound in a racemic or scalemic form, to obtain a carbonyl compound in scalemic form (epimerization). Or, the invention's process allows, starting from a carbonyl compound in a scalemic form, to obtain a carbonyl compound in a racemic form (racemization).

For the sake of clarity, by the term "photoredox catalyst", it is meant the normal meaning in the art, i.e. a catalyst absorbing light to accelerate a chemical reaction by activating of organic substrates via a single electron transfer process.

For the sake of clarity, by the expression "hydrogen atom transfer donor", it is meant the normal meaning in the art, i.e. a compound able to provide a hydrogen radical. Hydrogen atom transfer is also called HAT.

For the sake of clarity, by the term "carbonyl compound", it is meant the normal meaning in the art, i.e. a compound having a ketone or aldehyde functional group.

According to any above embodiment, the trisubstituted β position of the carbonyl compound is part of a ring.

According to any above embodiment, the carbonyl compound of the present invention is of formula

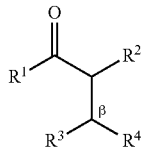
(I)

in a form of any one of its stereoisomers or a mixture thereof and wherein $R^1$ and $R^2$, simultaneously or independently, represent a hydrogen atom or a $C_{1-11}$ alkyl or a $C_{2-11}$ alkenyl or alkynyl group, optionally substituted; $R^3$ and $R^4$, simultaneously or independently, represent a $C_{1-11}$ alkyl or a $C_{2-11}$ alkenyl or alkynyl group, optionally substituted; or $R^1$ and $R^3$, taken together, represent a $C_{2-15}$ alkanediyl or alkenediyl group optionally substituted; or/and $R^2$ and $R^4$, taken together, represent a $C_{2-13}$ alkanediyl or alkenediyl group optionally substituted; or/and $R^3$ and $R^4$, taken together, represent a $C_{2-9}$ alkanediyl or alkenediyl group optionally substituted; provided that at least $R^1$ and $R^3$ or $R^2$ and $R^4$ are taken together.

For the sake of clarity, by the expression "any one of its stereoisomers or a mixture thereof", or the similar, it is meant the normal meaning understood by a person skilled in the art, i.e. that the compound of formula (I) can be a pure enantiomer or diastereomer. In other words, the compound of formula (I) may possess several stereocenters and each of said stereocenters can have two different stereochemistries (e.g. R or S). The compound of formula (I) may even be in the form of a pure enantiomer or in the form of a mixture of enantiomers or diastereoisomers. The compound of formula (I) can be in a racemic form or scalemic form. Therefore, the compound of formula (I) can be one stereoisomer or in the form of a composition of matter comprising, or consisting of, various stereoisomers.

It is understood that by " . . . $R^1$ and $R^3$, taken together, represent a $C_{2-15}$ linear, branched or cyclic alkanediyl group or/and $R^2$ and $R^4$, taken together, represent a $C_{2-15}$ linear, branched or cyclic alkanediyl group or/and $R^3$ and $R^4$, taken together . . . " or the similar, that said group could form a (poly)cyclic alkyl group. In other words compound (I) could be monocyclic or bicyclic, e.g. in the case wherein $R^1$ and $R^3$, as well as $R^3$ and $R^4$, are taken together, the compound of formula (II) comprises a bicyclic group such as a decalin, i.e. $R^1$, $R^3$ and $R^4$, taken together, represents an alkanetriyl.

According to a particular embodiment of the invention, the carbonyl compound is of formula

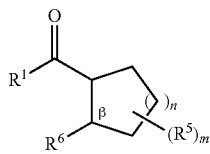
(II)

in a form of any one of its stereoisomers or a mixture thereof and wherein n is an integer between 1 and 11, m is an integer between 0 and 6, $R^1$ represents a hydrogen atom or a $C_{1-11}$ alkyl or a $C_{2-11}$ alkenyl or alkynyl group, optionally substituted; $R^6$ represents a $C_{1-11}$ alkyl or a $C_{2-11}$ alkenyl or alkynyl group, optionally substituted; $R^5$ group(s) represent substituent(s) of the saturated ring and are, independently of each other, a $C_{1-4}$ alkyl group or a $C_{2-4}$ alkenyl or alkynyl group optionally substituted and/or two $R^5$ groups, when taken together, represent a $C_{2-5}$ alkanediyl group optionally substituted.

According to any of the above embodiments, n may be an integer between 1 and 5. Particularly, n may be 1, 2 or 3. Even more particularly, n may be 2.

According to any of the above embodiments, m may be an integer between 0 and 4. Particularly, m may be 0, 1, 2 or 3.

According to any of the above embodiments, $R^1$ may be a hydrogen atom or a $C_{1-6}$ alkyl group or a $C_{2-6}$ alkenyl or alkynyl group. Particularly, $R^1$ may be a hydrogen atom or a $C_{1-6}$ alkyl group. Even more particularly, $R^1$ may be a hydrogen atom or a $C_{1-4}$ alkyl group. Even more particularly, $R^1$ may be a hydrogen atom or a methyl, ethyl or isopropyl group. Even more particularly, $R^1$ may be a hydrogen atom.

According to any of the above embodiments, $R^5$ groups represent a $C_{1-3}$ alkyl group or a $C_{2-3}$ alkenyl or alkynyl group. Particularly, $R^5$ groups represent a $C_{1-3}$ alkyl group. Particularly, $R^5$ groups represent a methyl or ethyl group. Particularly, $R^5$ group represent a methyl group.

According to any of the above embodiments, $R^6$ group represents a $C_{1-6}$ alkyl or a $C_{2-6}$ alkenyl or alkynyl group, optionally substituted. Particularly, $R^6$ group represents a $C_{1-4}$ alkyl group. Even more particularly, $R^6$ group represents a methyl or ethyl group.

According to a particular embodiment of the invention, the carbonyl compound is a cycloalkanone compound. Particularly, the carbonyl compound is of formula

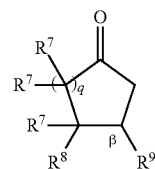
(III)

in a form of any one of its stereoisomers; wherein q is an integer between 1 and 13; $R^9$ represents $C_{1-11}$ alkyl group optionally substituted; each $R^7$ represent, independently of each other, a hydrogen atom or a $C_{1-4}$ alkyl or a $C_{2-4}$ alkenyl or alkynyl group optionally substituted; $R^8$ group represents, a hydrogen atom or a $C_{1-9}$ alkyl group optionally substituted; or $R^8$ and $R^9$ groups, when taken together, represent a $C_{2-9}$ alkanediyl group optionally substituted and/or $R^8$ and $R^7$ groups, when taken together, represent a $C_{2-9}$ alkanediyl group optionally substituted and/or $R^9$ and $R^7$ groups, when taken together, represent a $C_{2-9}$ alkanediyl group optionally substituted and/or two $R^7$ groups, when taken together, represent a $C_{2-9}$ alkanediyl group optionally substituted and/or three $R^7$ groups, when taken together, represent a $C_{4-9}$ alkanetriyl group optionally substituted.

According to any one of the above embodiments, $R^8$ group may represent, a hydrogen atom or a $C_{1-6}$ alkyl group optionally substituted. Particularly, $R^8$ group may represent, a hydrogen atom or a $C_{1-3}$ alkyl group optionally substituted. Even more particularly, $R^8$ group may represent, a hydrogen atom or a methyl or an ethyl group.

According to any one of the above embodiments, $R^9$ group may represent a $C_{1-6}$ alkyl group optionally substituted. Particularly, $R^9$ group may represent a $C_{1-3}$ alkyl group optionally substituted. Even more particularly, $R^9$ group may represent a methyl or an ethyl group.

According to any one of the above embodiments, $R^8$ and $R^9$ groups, when taken together, may represent a $C_{3-6}$ alkanediyl group optionally substituted.

According to any one of the above embodiments, the invention's process allows converting a cis or racemic bicyclic carbonyl compound into a trans bicyclic carbonyl compound or converting a trans or racemic bicyclic carbonyl compound into a cis bicyclic carbonyl compound, as herein shown:

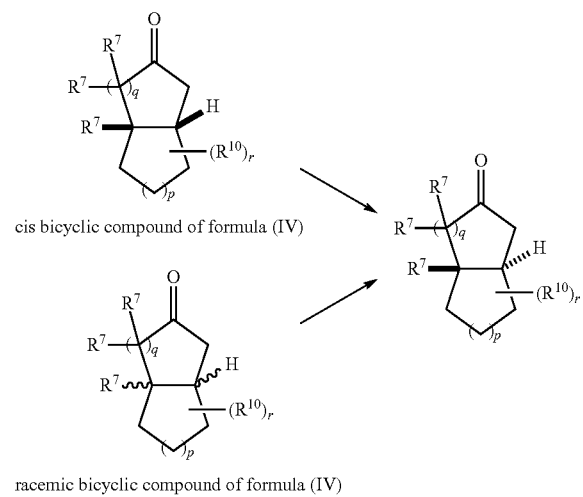

cis bicyclic compound of formula (IV)

racemic bicyclic compound of formula (IV)

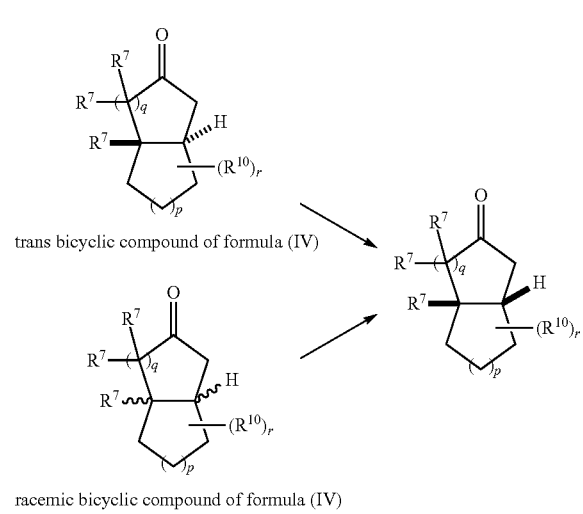

trans bicyclic compound of formula (IV)

racemic bicyclic compound of formula (IV)

Without be bound by theory, the invention's process allows obtaining the most thermodynamic stable compound which may be the cis or trans bicyclic carbonyl compound.

The cis bicyclic carbonyl compound or racemic bicyclic carbonyl compound or trans bicyclic carbonyl compound designate the relative configuration at the ring junction.

According to any one of the above embodiments, the carbonyl compound is of formula

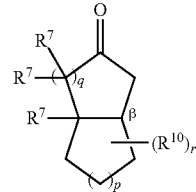

(IV)

in a form of any one of its stereoisomers; wherein q and p, independently of each other, are an integer between 1 and 3; r is an integer between 0 and 10, each $R^7$ represent a hydrogen atom or a $C_{1-4}$ alkyl or a $C_{2-4}$ alkenyl or alkynyl group optionally substituted; $R^{10}$ group(s) represent substituent(s) of the saturated ring and are, independently of each other, a $C_{1-4}$ alkyl group or a $C_{2-4}$ alkenyl or alkynyl group optionally substituted; or $R^7$ and $R^{10}$ groups, when taken together, represent a $C_{2-11}$ alkanediyl group and/or two $R^7$ groups, when taken together, represent a $C_{2-11}$ alkanediyl group optionally substituted and/or three $R^7$ groups, when taken together, represent a $C_{4-11}$ alkanetriyl group optionally substituted and/or two $R^{10}$ groups, when taken together, represent a $C_{2-11}$ alkanediyl group optionally substituted and/or three $R^{10}$ groups, when taken together, represent a $C_{4-11}$ alkanetriyl group optionally substituted.

According to any of the above embodiments, q may be 1 or 2. Particularly, q may be 2.

According to any of the above embodiments, p may be 1 or 2.

According to any of the above embodiments, r may be an integer between 0 and 6. Particularly, r may be an integer between 0 and 4. Even more particularly, r may be 0, 1, 2 or 3. Even more particularly, r may be 0, 1 or 2.

According to any of the above embodiments, $R^7$ groups may represent, independently of each other, a hydrogen atom or a $C_{1-3}$ alkyl or a $C_{2-3}$ alkenyl or alkynyl group optionally substituted. Even more particularly, $R^7$ may represent, a hydrogen atom or a methyl, tert-butyl, propyl or ethyl group. Particularly, $R^7$ groups may represent, independently of each other, a hydrogen atom, a methyl group or a propyl group. Even more particularly, at most four $R^7$ groups may represent a methyl group. Even more particularly, one $R^7$ group may represent a hydrogen atom, a methyl group or a propyl group and the others $R^7$ groups may represent a hydrogen atom.

According to any of the above embodiments, $R^{10}$ groups may represent, independently of each other, a $C_{1-3}$ alkyl or a $C_{2-3}$ alkenyl or alkynyl group optionally substituted. Even more particularly, $R^{10}$ groups may represent, independently of each other, a methyl, tert-butyl or ethyl group. Even more particularly, $R^{10}$ groups may represent, independently of each other, a methyl or ethyl group. Even more, particularly, $R^{10}$ groups may represent, when taken separately, independently of each other, a methyl group.

Particularly, the carbonyl compound is a decalone derivative. The invention's process is a process to convert a cis or racemic decalone derivative into a trans decalone derivative.

Particularly, the carbonyl compound is of formula

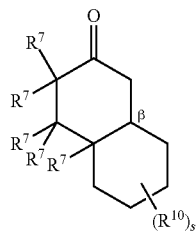

(V)

in a form of any one of its stereoisomers; wherein s is an integer between 0 and 8 and each $R^7$ and $R^{10}$ have the same meaning as above.

The optional substituents of $R^1$, $R^2$, $R^3$, $R^4$, $R^5$, $R^6$, $R^7$, $R^8$ $R^9$ and $R^{10}$ groups are one to two hydroxyl groups, $C_{1-3}$ alkyl groups, $C_{1-3}$ alkoxy groups, RCOO or ROCO groups wherein R is, independently from each other, a hydrogen atom or a $C_{1-4}$ alkyl group.

According to any one of the above embodiments, s may be an integer between 0 and 6. Particularly, s may be an integer between 0 and 4. Even more particularly, s may be 0, 1, 2 or 3.

Non-limiting examples of suitable carbonyl compound may include 2,2,3,6-tetramethylcyclohexane-1-carbaldehyde, 4a,8-dimethyloctahydronaphthalen-2(1H)-one, octahydronaphthalen-2(1H)-one, 7-ethyloctahydronaphthalen-2(1H)-one, 6-(tert-butyl)-3-methyloctahydronaphthalen-2(1H)-one, 7,8,8-trimethyloctahydronaphthalen-2(1H)-one, 8,8-dimethyloctahydronaphthalen-2(1H)-one, 4a-methyloctahydronaphthalen-2(1H)-one, 7a-propyloctahydro-5H-inden-5-one, 3-methylcyclohexan-1-one or −5,5-dimethyloctahydronaphthalen-2(1H)-one.

According to any one of the above embodiments, the photoredox catalyst may be a metal complex photoredox catalyst, a metal-free photoredox catalyst or an organic dye.

The metal complex photoredox catalyst may be an iridium, a copper or a ruthenium based complex. Particularly, the metal complex photoredox catalyst may be of formula

[M(L)(L')(L")]Z_n (VI)

wherein M is iridium or ruthenim, L, L' and L" are, independently of each other, 2,2'-bipyridine or 2-phenylpyridine optionally substituted with one to six hydroxy groups, $C_{1-4}$ alkyl group, $C_{1-3}$ alkoxyl group, halogen atoms or halo- or perhalo hydrocarbon; Z represents a non-coordinated anion, n is 0 or 1 when M is iridium and n is 2 when M is ruthenium.

By "halo- or perhalo-hydrocarbon" it is meant a hydrocarbon group substituted with halogen atoms such as $CF_3$ or $CClH_2$.

According to any one of the above embodiments; L, L' and L" may be, independently of each other, 2,2'-bipyridine or 2-phenylpyridine optionally substituted with one to four hydroxy groups, $C_{1-4}$ alkyl group, $C_{1-3}$ alkoxyl group, halogen atoms or halo- or perhalo hydrocarbon. Particularly, L, L' and L" may be 2,2'-bipyridine or 2-phenylpyrine optionally substituted with one to four methyl, methoxy, trifluoromethyl or tertbutyl group or fluorine atom. Non-limiting examples of suitable L, L' and L" may include 2,2'-bipyridine, 2-phenylpyridine, 4,4'-dimethoxy-2,2'-bipyridine, 4,4'-di-tert-butyl-2,2'-bipyridine, 2-(2,4-difluorophenyl)-5-methoxypyridine, 2-(4-fluorophenyl)-5-methoxypyridine, 5-methyl-2-(p-tolyl)pyridine, 2-(4-fluorophenyl)-5-methylpyridine, 2-(p-tolyl)-5-(trifluoromethyl)pyridine, 2-(4-fluorophenyl)-5-(trifluoromethyl)pyridine or 2-(2,4-difluorophenyl)-5-(trifluoromethyl)pyridine.

According to any one of the above embodiments; Z represents $ClO_4^-$, $R'SO_3^-$, wherein R' is a chlorine or fluoride atom or an $C_1$-$C_8$ fluoroalkyl or fluoroaryl group, $BF_4^-$, $PF_6^-$, $SbCl_6^-$, $SbF_6^-$, or $BR''_4^-$, wherein R" is a phenyl group optionally substituted by one to five groups such as halogen atoms or methyl or $CF_3$ groups. Particularly, Z may be $BF_4^-$, $PF_6^-$, $ClO_4^-$, $C_6F_5SO_3^-$, $BPh_4^-$, $CF_3SO_3^-$ or $B[3,5-(CF_3)_2C_6H_4]_4^-$, even more particularly $PF_6^-$.

According to a particular embodiment, non-limiting examples of suitable photoredox catalyst may include eosin Y, fluorescein, 2,4,5,6-tetra(9H-carbazol-9-yl)isophthalonitrile (corresponding to 4CzIPN), rose bengal, 10-(3,5-dimethoxyphenyl)-9-mesityl-1,3,6,8-tetramethoxyacridin-10-ium tetrafluoroborate (corresponding to Mes-Acr-4), tris[4,4'-Bis(1,1-dimethylethyl)-2,2'-bipyridine-N1,N1'] Ruthenium$^{(II)}$ hexafluorophosphate (corresponding to Ru(bpy)$_3$(PF$_6$)$_2$), Tris[2-phenylpyridinato-C$^2$,N]Iridium$^{(III)}$ (corresponding to Ir(ppy)$_3$), [4,4'-Bis(1,1-dimethylethyl)-2,2'-bipyridine-N1,N1']bis[2-pyridinyl-N]phenyl-C] Iridium$^{(III)}$ hexafluorophosphate (corresponding to Ir(ppy)$_2$(dtbbpy)PF$_6$), [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium$^{(III)}$ hexafluorophosphate (corresponding to Ir(dF(CF3)ppy)$_2$(dtbbpy)PF$_6$), [4,4'-Bis(1,1-dimethylethyl)-2,2'-bipyridine-κN1,κN1']bis[3,5-difluoro-2-[5-(methyl)-2-pyridinyl-κN]phenyl-κC]Iridium$^{(III)}$ hexafluorophosphate (corresponding to Ir(dF(Me)ppy)$_2$(dtbbpy)PF$_6$), [4,4'-Bis(1,1-dimethylethyl)-2,2'-bipyridine-κN1,κN1']bis[3,5-difluoro-2-[2-pyridinyl-κN]phenyl-κC] Iridium$^{(III)}$ hexafluorophosphate (corresponding to Ir(dFppy)$_2$(dtbbpy)PF$_6$) or [4,4'-Bis(1,1-dimethylethyl)-2,2'-bipyridine-κN1,κN1']bis[3-fluoro-5-trifluoromethyl-2-[5-(trifluoromethyl)-2-pyridinyl-κN]phenyl-κC]Iridium$^{(III)}$ hexafluorophosphate (corresponding to Ir(FCF$_3$(CF$_3$)ppy)$_2$(dtbbpy)PF$_6$). Particularly, the photoredox catalyst may be [4,4'-Bis(1,1-dimethylethyl)-2,2'-bipyridine-N1,N1']bis[2-pyridinyl-N]phenyl-C]Iridium$^{(III)}$ hexafluorophosphate (corresponding to Ir(ppy)$_2$(dtbbpy)PF$_6$) or 2,4,5,6-tetra(9H-carbazol-9-yl)isophthalonitrile (corresponding to 4CzIPN).

According to any one of the above embodiments, the photoredox catalyst can be added into the reaction medium of the invention's process in a large range of concentrations. As non-limiting examples, one can cite as photoredox catalyst concentration values those ranging from about 0.001 mol % to about 10 mol %, relative to the amount of the carbonyl compound, particularly from about 0.005 mol % to about 5 mol %, relative to the amount of the carbonyl compound, even more particularly, from about 0.01 mol % to about 1 mol %, relative to the amount of the carbonyl compound. The optimum concentration of the catalyst will depend, as the person skilled in the art knows, on the nature of the latter, on the nature of the carbonyl compound, the hydrogen atom transfer donor and/or the secondary amine, on the reaction temperature as well as on the desired time of reaction.

According to any one of the above embodiments, the hydrogen atom transfer donor may be any hydrogen atom transfer donor used in radical chemistry such metal hydride compounds such as tin, silicon, sulfur, selenium, boron or phosphorous derivatives or organic compounds such as malonitrile or cyclohexadiene derivatives such as cyclohexa-1,4-diene or gamma-terpinene.

According to a particular embodiment, the hydrogen atom transfer donor is a sulfur derivative, such as a thiol compound, particularly an aromatic thiol. Particularly, the hydrogen atom transfer donor is a thiophenol derivative of formula

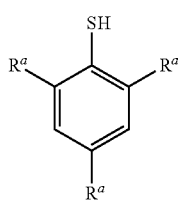

(VII)

wherein each $R^a$ represents, independently from each other, a hydrogen atom, a halogen atom, a $C_{1-2}$ linear alkyl group, a $C_{3-4}$ linear or branched alkyl group, a phenyl group optionally substituted by one to five halogen atoms and/or $C_{1-4}$ alkyl or alkoxyl groups or a silyl group trisubstituted with $C_{1-4}$ alkyl groups or an aryl groups. Particularly, the thiophenol derivative may be selected from the group consisting of benzenethiol, 2,4,6-trimethylbenzenethiol, 2,4,6-tri-iso-propylbenzenethiol, 2,6-dimethylbenzenethiol, 2,6-di-tert-butyl-4-methylbenzenethiol, 2,6-diisopropylbenzenethiol, 2,4,6-tri-tert-butylbenzenethiol, 4-tert-butylbenzenethiol and 4-fluorobenzenethiol. Particularly, the thiophenol derivative may be selected from the group consisting of benzenethiol, 2,4,6-trimethylbenzenethiol, 2,4,6-tri-iso-propylbenzenethiol, 2,6-dimethylbenzenethiol, 2,4,6-tri-tert-butylbenzenethiol, 4-tert-butylbenzenethiol and 4-fluorobenzenethiol. Particularly, the thiophenol derivative may be selected from the group consisting of benzenethiol, 2,6-dimethylbenzenethiol, 2,4,6-trimethylbenzenethiol, 2,6-di-tert-butyl-4-methylbenzenethiol, 2,6-diisopropylbenzenethiol, 2,4,6-tri-iso-propylbenzenthiol and 2,4,6-tri-tert-butylbenzenthiol Even more particularly, the thiophenol derivative may be benzenethiol or 2,4,6-tri-iso-propylbenzenthiol. Even more particularly, the thiophenol derivative may be benzenethiol.

According to any one of the above embodiments, the thiophenol can be added into the reaction medium of the invention's process in a large range of concentrations. As non-limiting examples, one can cite as thiophenol concentration values those ranging from about 0.5 mol % to about 50 mol %, relative to the amount of the carbonyl compound, particularly from about 1 mol % to about 30 mol %, relative to the amount of the carbonyl compound, even more particularly, from about 5 mol % to about 25 mol %, relative to the amount of the carbonyl compound. The optimum concentration of the thiophenol will depend, as the person skilled in the art knows, on the nature of the latter, on the nature of the aldehyde, the olefin, the photoredox catalyst and/or the secondary amine, on the reaction temperature as well as on the desired time of reaction.

According to any one of the above embodiments, the amine is a primary or a secondary amine. Particularly, the amine is a secondary amine.

By the term "primary or secondary amine", it is meant the normal meaning in the art, i.e. the nitrogen atom is substituted by two hydrogen atom and one group different than hydrogen atom for primary amine and by one hydrogen atom and two groups different than hydrogen atom for secondary amine.

The secondary amine may be a cyclic or acyclic amine optionally substituted by one to three halogen atoms or an acid or ester group. Said secondary amine may be in the form of ammonium salt. Particularly, the secondary amine may be selected from the group consisting of pyrrolidine, piperidine, azepane, 2-(bis(3,5-bis(trifluoromethyl)phenyl)((trimethylsilyl)oxy)methyl)pyrrolidine, 2,2,2-trifluoro-N-methylethan-1-amine, 2,2,2-trifluoro-N-methylethan-1-aminium chloride, 2,2,2-trifluoro-N-ethylethan-1-amine, 2,2,2-trifluoro-N-ethylethan-1-aminium chloride, bis(2-chloroethyl)amine, bis(2-chloroethyl)aminium chloride, dimethyl amine and dimethylammonium chloride. Particularly, the secondary amine may be selected from the group consisting of pyrrolidine, piperidine, azepane, 2-(bis(3,5-bis(trifluoromethyl)phenyl)((trimethylsilyl)oxy)methyl)pyrrolidine, 2,2,2-trifluoro-N-methylethan-1-amine, 2,2,2-trifluoro-N-methylethan-1-aminium chloride, bis(2-chloroethyl)amine, bis(2-chloroethyl)aminium chloride, dimethyl amine and dimethylammonium chloride. Even more particularly, the secondary amine may be pyrrolidine, piperidine, azepane. Even more particularly, the secondary amine may be pyrrolidine, or azepane.

According to any one of the above embodiments, the secondary amine can be added into the reaction medium of the invention's process in a large range of concentrations. As non-limiting examples, one can cite as secondary amine concentration values those ranging from about 0.5 mol % to about 20 mol %, relative to the amount of the aldehyde, particularly from about 5 mol % to about 15 mol %, relative to the amount of the aldehyde. The optimum concentration of the secondary amine will depend, as the person skilled in the art knows, on the nature of the latter, on the nature of the aldehyde, the olefin, the photoredox catalyst and/or the hydrogen atom transfer donor, on the reaction temperature as well as on the desired time of reaction.

According to any one of the above embodiments, the light may have a wavelength comprised in the range between 250 nm and 800 nm. Particularly, the light may be UV visible light. Said light may be generated by LED lamp or LED strip.

The reaction can be carried out in the presence or absence of a solvent. When a solvent is required or used for practical reasons, then any solvent current in such reaction type can be used for the purposes of the invention. Solvents with high dielectric constant are preferred. Non-limiting examples of solvents include DMSO, DMPU, DMF, DMA, NMP, acetonitrile, DME, methyl tetrahydrofuran or mixtures thereof. The choice of the solvent is function of the nature of the substrates and/or catalyst and the person skilled in the art is well able to select the solvent most suitable in each case to optimize the reaction.

The invention's process can be carried out at a temperature in the range comprised between 0° C. and 50° C., more particularly, the invention's process can be carried out at room temperature; i.e. around 25° C. Of course, a person skilled in the art is also able to select the preferred temperature according to the melting and boiling point of the starting and final products as well as the desired time of reaction or conversion.

The invention's process can be carried out under batch or continuous conditions.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 400 or 500 MHz machine for $^1H$ and $^{13}C$, the chemical shifts δ are indicated in ppm with respect to TMS as standard, the coupling constants J are expressed in Hz.

Example 1

Isomerisation of (4aRS,8RS,8aRS)-4a,8-dimethyl-octahydronaphthalen-2(1H)-one into (4aRS,8RS, 8aSR)-4a,8-dimethyloctahydronaphthalen-2(1H)-one Under argon, to a solution of (4,4'-Di-t-butyl-2,2'-bipyridine)bis[2-(2-pyridinyl-kN)phenyl-kC]iridium(III) hexafluorophosphate (4 mg, 0.004 mmol) in DMPU (0.5 mL) was added rac-(4aR,8R)-4a,8-dimethyloctahydronaphthalen-2(1H)-one (7.22 g, 38.9 mmol, ratio cis/trans 53/47), pyrrolidine (0.14 g, 1.92 mmol) and benzenethiol (0.42 g, 3.85 mmol) in a schlenk. The mixture was stirred at room temperature and irradiated under Blue Light strip for 24 hours to yield the desired high isomerized decalone (ratio cis/trans 13/87). The reaction mixture was diluted with EtOAc and washed with brine. The organic layer was dried over anhydrous MgSO4, filtered and concentrated under reduced pressure. A bulb to bulb distillation gave the desired rac-(4aR,8R)-4a,8-dimethyloctahydronaphthalen-2(1H)-one (6.45 g, 35.77 mmol, ratio cis/trans 13/87, 92% yield).

$^1H$ NMR (500 MHz, $CDCl_3$): 0.81 (d, J=6.5 Hz, 3H), 0.89-0.98 (m, 1H), 1.04 (s, 3H), 1.08-1.10 (m, 2H), 1.35-1.73 (m, 7H), 2.00 (t, J=15.0 Hz, 1H), 2.26-2.33 (m, 1H), 2.43-2.51 (m, 2H).

$^{13}C$ NMR (125 MHz, $CDCl_3$): 212.2 (C), 50.8 (CH), 41.5 (CH2), 41.0 (CH2), 40.6 (CH2), 38.1 (CH2), 35.7 (CH2), 33.3 (C), 32.4 (CH), 21.4 (CH2), 19.7 (CH3), 16.0 (CH3).

Example 2

Isomerisation of (4aRS,6RS,8aRS)-6-ethyloctahydronaphthalen-2(1H)-one into (4aRS,6RS,8aSR)-6-ethyloctahydronaphthalen-2(1H)-one To a solution of (4,4'-Di-t-butyl-2,2'-bipyridine)bis[2-(2-pyridinyl-kN)phenyl-kC]iridium(III) hexafluorophosphate (11 mg, 0.01 mmol) in DMPU (1 mL) was added rac-(4aR,6R,8aR)-6-ethyldecalin-2-one (3.57 g, 19.82 mmol, ratio cis/trans 86/14), pyrrolidine (76 mg, 1.07 mmol) and 2,4,6-tri-isopropylbenzenethiol (481 mg, 2.03 mmol). The mixture was stirred at room temperature and irradiated under Blue Light (Kessil Lamp) for 8 hours to yield the high isomerized decalone (ratio cis/trans 2/98). The reaction mixture was diluted with EtOAc and washed with brine. The organic layer was dried over anhydrous MgSO4, filtered and concentrated under reduced pressure. A column chromatography on silica gel (eluent heptane/EtOAc 95/5) and a bulb to bulb distillation gave the desired rac-(4aR,6R,8aS)-6-ethyldecalin-2-one (2.50 g, 12.89 mmol, ratio cis/trans 2/98, 65% yield).

$^1H$ NMR (500 MHz, $CDCl_3$): 0.62-0.70 (m, 1H), 0.84-0.93 (m, 1H), 0.89 (t, J=7.4 Hz, 3H), 1.08-1.17 (m, 1H), 1.21-1.45 (m, 6H), 1.65-1.72 (m, 1H), 1.74-1.82 (m, 2H), 1.93-1.98 (m, 1H), 2.05 (t, J=13.3 Hz, 1H), 2.26-2.41 (m, 3H).

$^{13}C$ NMR (125 MHz, $CDCl_3$): 211.9 (C), 48.5 (CH2), 43.4 (CH), 41.5 (CH2), 41.4 (CH), 39.3 (CH), 39.0 (CH2), 34.1 (CH2), 33.6 (CH2), 31.9 (CH2), 29.8 (CH2), 11.5 (CH3).

Example 3

Isomerisation of (4aRS,8aSR)-octahydronaphthalen-2(1H)-one into (4aRS,8aRS)-octahydronaphthalen-2(1H)-one To a solution of (4,4'-Di-t-butyl-2,2'-bipyridine)bis[2-(2-pyridinyl-kN)phenyl-kC]iridium(III) hexafluorophosphate (4.7 mg, 0.005 mmol) in DMPU (2 mL) was added octahydronaphthalen-2(1H)-one (76.6 mg, 0.50 mmol, ratio cis/trans 79/21), pyrrolidine (7.1 mg, 0.10 mmol) and benzenethiol (11 mg, 0.10 mmol). The mixture was stirred at room temperature and irradiated under Blue Light strip for 24 hours to yield the high isomerized octahydronaphthalen-2(1H)-one up to a ratio cis/trans 4/96.

$^{13}C$ NMR (90 MHz, $CDCl_3$): 211.3 (C), 48.7 (CH2), 43.5 (CH), 41.8 (CH), 41.6 (CH2), 34.3 (CH2), 33.7 (CH2), 32.8 (CH2), 26.2 (CH2), 25.7 (CH2).

Example 4

Isomerisation of (4aSR,8aRS)-5,5-dimethyloctahydronaphthalen-2(1H)-one into (4aSR,8aSR)-5,5-dimethyloctahydronaphthalen-2(1H)-one Under argon, to a solution of (4,4'-Di-t-butyl-2,2'-bipyridine)bis[2-(2-pyridinyl-kN)phenyl-kC]iridium(III) hexafluorophosphate (7.8 mg, 0.008 mmol) in DMPU (5 mL) was added rac-(4aR,8aS)-5,5-dimethyldecalin-2-one (4.0 g, 22.2 mmol, ratio cis/trans 97/3), pyrrolidine (0.16 g, 2.2 mmol) and 2,4,6-tri-isopropylbenzenethiol (0.52 g, 2.2 mmol). The mixture was stirred at room temperature and irradiated under Blue Light in Merck photoreactor for 24 hours to yield the high isomerized decalone (ratio cis/trans 7/93). The reaction mixture was diluted with EtOAc and washed with brine. The organic layer was dried over anhydrous MgSO4, filtered and concentrated under reduced pressure. A column chromatography on silica gel (eluent heptane/MTBE 98/2) gave the desired rac-(4aR,6R,8aS)-6-ethyldecalin-2-one (2.14 g, 11.9 mmol, ratio cis/trans 1/99, 53% yield).

$^1H$ NMR (400 MHz, $CDCl_3$): 0.81 (s, 3H), 0.98 (s, 3H), 1.00-1.70 (m, 9H), 2.02 (t, J=13 Hz, 1H), 2.07-2.12 (m, 1H), 2.25-2.43 (m, 3H).

$^{13}C$ NMR (100 MHz, $CDCl_3$): 211.7 (C), 50.2 (CH), 49.1 (CH2), 42.0 (CH2), 41.8 (CH2), 38.5 (CH), 35.3 (CH2), 33.1 (C), 30.6 (CH3), 26.9 (CH2), 21.8 (CH2), 19.9 (CH3).

Example 5

Isomerisation of (4aRS,8RS,8aRS)-4a,8-dimethyl-octahydronaphthalen-2(1H)-one into (4aRS,8RS, 8aSR)-4a,8-dimethyloctahydronaphthalen-2(1H)-one Using Various Amines The isomerization has been performed as reported in Example 1.

TABLE 1

Isomerization using various amines

| Entry | Amine | cis/trans |
|---|---|---|
| 1 | azepane | 12/88 |
| 2 | piperidine | 32/68 |
| 3 | pyrrolidine | 12/88 |
| 4 | — | 53/47 |

Example 6

Isomerisation of (4aRS,8RS,8aRS)-4a,8-dimethyl-octahydronaphthalen-2(1H)-one into (4aRS,8RS,8aSR)-4a,8-dimethyloctahydronaphthalen-2(1H)-one Using Various Inorganic Photoredox Catalyst The isomerization has been performed as reported in Example 1.

TABLE 2

Isomerization using various inorganic photoredox catalyst

| Entry | Photocatalyst (mol %) | Amine | DMPU | cis/trans |
|---|---|---|---|---|
| 1 | Ir(ppy)$_3$ (1) | azepane | 0.25 | 22/78 |
| 2 | | pyrrolidine | 0.25 | 24/76 |
| 3 | | piperidine | 0.25 | 41/59 |
| 4 | Ir(ppy)$_3$ (0.1) | pyrrolidine | — | 24/76 |
| 5 | Ru(bpy)$_3$(PF$_6$)$_2$ (1) | azepane | 0.25 | 23/77 |
| 6 | Ru(bpy)$_3$(PF$_6$)$_2$ (1) | pyrrolidine | 0.25 | 12/88 |

Example 7

Isomerisation of (4aRS,8RS,8aRS)-4a,8-dimethyl-octahydronaphthalen-2(1H)-one into (4aRS,8RS,8aSR)-4a,8-dimethyloctahydronaphthalen-2(1H)-one Using Various Organic Photoredox Catalyst The isomerization has been performed as reported in Example 1.

TABLE 3

Isomerization using various organic photoredox catalyst

| Entry | Photocata. (mol %) | Amine | solvent | cis/trans |
|---|---|---|---|---|
| 1 | Eosin Y (10) | pyrrolidine | DMPU | 34/66 |
| 2 | Fluorescein (10) | pyrrolidine | DMPU | 30/70 |
| 3 | | pyrrolidine | DMF | 32/68 |
| 4 | | azepane | DMPU | 39/61 |
| 5 | Fluorescein (5) | pyrrolidine | DMPU | 18/82 |
| 6 | Fluorescein (1) | pyrrolidine | DMPU | 24/76 |
| 7 | 2,4,5,6-tetra(9H-carbazol-9-yl)isophthalonitrile (0.25) | pyrrolidine | — | 12/88 |

Example 8

Isomerisation of (4aRS)-8,8-dimethyloctahydronaphthalen-2(1H)-one into (4aRS,8aRS)-8,8-dimethyloctahydronaphthalen-2(1H)-one To a solution of (4,4'-Di-t-butyl-2,2'-bipyridine)bis[2-(2-pyridinyl-kN)phenyl-kC]iridium(III) hexafluorophosphate (2.5 mg, 0.003 mmol) in DMPU (1 mL) was added (4aR)-8,8-dimethyloctahydronaphthalen-2(1H)-one (901.5 mg, 5 mmol, ratio cis/trans 19/81), pyrrolidine (17.8 mg, 0.25 mmol) and benzenethiol (55.1 mg, 0.5 mmol). The mixture was stirred at room temperature and irradiated with Kessil Blue lamp for 24 hours. The crude reaction mixture was diluted with water and extracted with MTBE. The organic layer was dried over anhydrous magnesium sulfate and concentrated with rotavap. The crude product was distilled to yield (4aRS,8aRS)-8,8-dimethyloctahydronaphthalen-2(1H)-one up to a ratio cis/trans 2/98 (840 mg, 4.66 mmol, 93% yield).

$^{13}$C NMR (125 MHz, CDCl$_3$): 213.0 (C), 51.8 (CH), 42.1 (CH2), 41.5 (CH2), 41.3 (CH2), 36.2 (CH), 34.2 (CH2), 33.6 (CH2), 33.4 (C), 29.9 (CH3), 21.6 (CH2), 19.6 (CH3).

Example 9

Isomerisation of (7aSR)-7a-propyloctahydro-5H-inden-5-one into (3aRS,7aSR)-7a-propyloctahydro-5H-inden-5-one To a solution of (4,4'-Di-t-butyl-2,2'-bipyridine)bis[2-(2-pyridinyl-kN)phenyl-kC]iridium(III) hexafluorophosphate (3.7 mg, 0.004 mmol) in DMPU (1 mL) was added (7aS)-7a-propyloctahydro-5H-inden-5-one (1.00 g, 5.55 mmol, ratio cis/trans 56/44), pyrrolidine (32 mg, 0.45 mmol) and benzenethiol (73 mg, 0.66 mmol). The mixture was stirred at room temperature and irradiated with Kessil Blue lamp for 24 hours. The crude reaction mixture was diluted with water and extracted with MTBE. The organic layer was dried over anhydrous magnesium sulfate and concentrated with rotavap. The crude product was distilled to yield (3aRS,7aSR)-7a-propyloctahydro-5H-inden-5-one up to a ratio cis/trans 99/1 (800 mg, 4.44 mmol, 80% yield).

$^{13}$C NMR (125 MHz, CDCl$_3$): 214 (C), 45.5 (CH), 42.7 (C), 42.3 (CH2), 41.9 (CH2), 37.1 (CH2), 36.5 (CH2), 32.6 (CH2), 30.4 (CH2), 22.4 (CH2), 18.0 (CH2), 15.0 (CH3).

Example 10

Racemisation of (R)-3-methylcyclohexan-1-one into 3-methylcyclohexan-1-one

In a glass vial, pyrrolidine (18.9 mg, 0.26 mmol), benzenethiol (57.8 mg, 0.52 mmol), (R)-3-methylcyclohexan-1-one (562.4 mg, 5.01 mmol, ee>99%) were mixed with a solution of (4,4'-Di-t-butyl-2,2'-bipyridine)bis[2-(2-pyridinyl-kN)phenyl-kC]iridium(III) hexafluorophosphate (2.4 mg, 0.003 mmol) in DMPU (1 mL). The mixture was stirred at room temperature and irradiated with Kessil Blue lamp for 24 hours. Analysis on GC with chiral column (Mega Dex DET Beta) showed that the racemic 3-methylcyclohexan-1-one was obtained.

The invention claimed is:

1. A process comprising isomerizing a β-trisubstituted C$_3$-C$_{70}$ carbonyl compound to modify the configuration of the trisubstituted β position, characterized in that said process is carried out in the presence of a photoredox catalyst, a hydrogen atom transfer donor, an amine and light.

2. The process according to claim 1, characterized in that the trisubstituted β position of the carbonyl compound is part of a ring.

3. The process according to claim 1, characterized in that the carbonyl compound is of formula

(I)

in a form of any one of its stereoisomers or a mixture thereof and wherein R$^1$ and R$^2$, simultaneously or independently, represent a hydrogen atom or a C$_{1-11}$ alkyl or a C$_{2-11}$ alkenyl or alkynyl group, optionally substituted; R³ and R⁴, simultaneously or independently, represent a $C_{1-11}$ alkyl or a $C_{2-11}$ alkenyl or alkynyl group, optionally substituted; or/and R³, taken together, represent a $C_{2-15}$ alkanediyl or alkenediyl group optionally substituted; or R¹ and R² and R⁴, taken together, represent a $C_{2-13}$ alkanediyl or alkenediyl group optionally substituted; or/and R³ and R⁴, taken together, represent a $C_{2-9}$ alkanediyl or alkenediyl group optionally substituted; provided that at least R¹ and R³ or R² and R⁴ are taken together.

4. The process according to claim 1, characterized in that the carbonyl compound is of formula

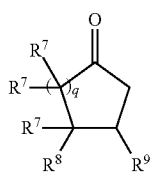

(III)

in a form of any one of its stereoisomers; wherein q is an integer between 1 and 13; R⁹ represents $C_{1-11}$ alkyl group optionally substituted; each R⁷ represent, independently of each other, a hydrogen atom or a $C_{1-4}$ alkyl or a $C_{2-4}$ alkenyl or alkynyl group optionally substituted; R⁸ group represents, a hydrogen atom or a $C_{1-9}$ alkyl group optionally substituted; or R⁸ and R⁹ groups, when taken together, represent a $C_{2-9}$ alkanediyl group optionally substituted and/or R⁸ and R⁷ groups, when taken together, represent a $C_{2-9}$ alkanediyl group optionally substituted and/or R⁹ and R⁷ groups, when taken together, represent a $C_{2-9}$ alkanediyl group optionally substituted and/or two R⁷ groups, when taken together, represent a $C_{2-9}$ alkanediyl group optionally substituted and/or three R⁷ groups, when taken together, represent a $C_{4-9}$ alkanetriyl group optionally substituted.

5. The process according to claim 4, characterized in that the carbonyl compound is of formula

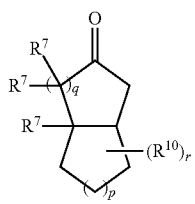

(IV)

in a form of any one of its stereoisomers; wherein q and p, independently of each other, are an integer between 1 and 3; r is an integer between 0 and 10, each R⁷ represent a hydrogen atom or a $C_{1-4}$ alkyl or a $C_{2-4}$ alkenyl or alkynyl group optionally substituted; R¹⁰ group(s) represent substituent(s) of the saturated ring and are, independently of each other, a $C_{1-4}$ alkyl group or a $C_{2-4}$ alkenyl or alkynyl group optionally substituted; or R⁷ and R¹⁰ groups, when taken together, represent a $C_{2-11}$ alkanediyl group and/or two R⁷ groups, when taken together, represent a $C_{2-11}$ alkanediyl group optionally substituted and/or three R⁷ groups, when taken together, represent a $C_{4-11}$ alkanetriyl group optionally substituted and/or two R¹⁰ groups, when taken together, represent a $C_{2-11}$ alkanediyl group optionally substituted and/or three R¹⁰ groups, when taken together, represent a $C_{4-11}$ alkanetriyl group optionally substituted.

6. The process according to claim 5, characterized in the carbonyl compound is of formula

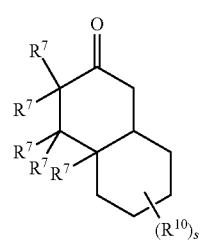

(V)

in a form of any one of its stereoisomers; wherein s is an integer between 0 and 8.

7. The process according to claim 4, characterized in that the R⁷ groups represent, independently of each other, a hydrogen atom or a methyl or propyl group.

8. The process according to claim 5, characterized in that the R¹⁰ groups represent, independently of each other, a methyl or ethyl group.

9. The process according to claim 1, characterized in that the photoredox catalyst is a metal complex photoredox catalyst, a metal-free photoredox catalyst or an organic dye.

10. The process according to claim 1, characterized in that the metal complex photoredox catalyst is an iridium, a copper or a ruthenium based complex.

11. The process according to claim 1, characterized in that the photoredox catalyst is of formula

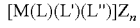

[M(L)(L')(L'')]$Z_n$ (VI)

wherein M is iridium or ruthenim, L, L' and L'' are, independently of each other, 2,2'-bipyridine or 2-phenylpyridine optionally substituted with one to six hydroxy groups, $C_{1-4}$ alkyl group, $C_{1-3}$ alkoxyl group, halogen atoms or halo- or perhalo hydrocarbon; Z represents a non-coordinated anion, n is 0 or 1 when M is iridium and n is 2 when M is ruthenium.

12. The process according to claim 1, characterized in that the hydrogen atom transfer donor is a thiol compound.

13. The process according to claim 1, characterized in that the amine is a secondary amine.

14. The process according to claim 1, characterized in that the hydrogen atom transfer donor is an aromatic thiol.

15. The process according to claim 1, characterized in that the hydrogen atom transfer donor is benzethiol or 2,4,6-trisiopropylbenzenethiol.

* * * * *